United States Patent
Zhang et al.

(10) Patent No.: US 8,131,365 B2
(45) Date of Patent: Mar. 6, 2012

(54) EVENT-BASED BATTERY MONITOR FOR IMPLANTABLE DEVICES

(75) Inventors: Cheng Zhang, Vadnais Heights, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 234 days.

(21) Appl. No.: 12/492,416

(22) Filed: Jun. 26, 2009

(65) Prior Publication Data

US 2010/0010559 A1   Jan. 14, 2010

Related U.S. Application Data

(60) Provisional application No. 61/079,253, filed on Jul. 9, 2008.

(51) Int. Cl.
*A61N 1/00* (2006.01)

(52) U.S. Cl. ........................................................ 607/27

(58) Field of Classification Search .................. 320/136; 340/10.1; 607/27, 29, 62, 63
See application file for complete search history.

(56) References Cited

U.S. PATENT DOCUMENTS

| | | | |
|---|---|---|---|
| 6,108,579 A | 8/2000 | Snell et al. | |
| 6,433,513 B1 | 8/2002 | Hayashi | |
| 6,671,552 B2 | 12/2003 | Merritt et al. | |
| 7,058,451 B2 | 6/2006 | Obel et al. | |
| 7,469,161 B1 | 12/2008 | Gandhi et al. | |
| 7,620,452 B1 | 11/2009 | Russie | |
| 2003/0065366 A1 | 4/2003 | Merritt et al. | |
| 2003/0181953 A1 | 9/2003 | Dropps et al. | |
| 2005/0017685 A1 | 1/2005 | Rees et al. | |
| 2007/0142727 A1 | 6/2007 | Zhang et al. | |
| 2007/0179549 A1 | 8/2007 | Russie | |
| 2007/0250126 A1 | 10/2007 | Maile et al. | |
| 2009/0312650 A1 | 12/2009 | Maile | |
| 2010/0274302 A1* | 10/2010 | Armstrong et al. | 607/2 |

FOREIGN PATENT DOCUMENTS

| | | |
|---|---|---|
| WO | 2006014971 A2 | 2/2006 |
| WO | 2007089392 A2 | 8/2007 |
| WO | 2008121110 A1 | 10/2008 |

OTHER PUBLICATIONS

International Search Report and Written Opinion issued in PCT/US2009/048779, 18 pages.

* cited by examiner

*Primary Examiner* — George Manuel
*Assistant Examiner* — Robert Wieland
(74) *Attorney, Agent, or Firm* — Faegre Baker Daniels LLP (57) ABSTRACT

A remaining charge capacity of a battery having an initial charge capacity is monitored. The battery powers a remote implantable medical device (IMD) that includes an active state, during which the remote IMD performs at least one function, and an inactive state, during which the remote IMD performs no functions. An active state charge consumption is computed based on stored parameters associated with an operational charge consumption for each function, and an inactive state charge consumption is computed based on a leakage current associated with the inactive state and a time the remote IMD is in the inactive state. The active state charge consumption and inactive state charge consumption are subtracted from the initial charge capacity to determine the remaining charge capacity.

13 Claims, 4 Drawing Sheets

EVENT-BASED BATTERY MONITOR FOR IMPLANTABLE DEVICES

CROSS-REFERENCE TO RELATED APPLICATION

This application claims priority to Provisional Application No. 61/079,253, filed Jul. 9, 2008, which is herein incorporated by reference in its entirety.

TECHNICAL FIELD

The present invention relates to electrical energy storage in medical devices. More specifically, the invention relates to systems and methods for determining a remaining charge in a battery associated with a medical device.

BACKGROUND

Batteries have limited life spans. When the charge is depleted in a battery, the battery-powered device will cease to function. To circumvent loss of functionality, the battery must be replaced or recharged prior to charge depletion. Accurate determination of a battery's state of depletion is particularly important for battery-powered medical devices that are implanted in human patients. With an accurate determination of battery depletion state, an implanted medical device may be recharged or replaced in order to maintain monitoring and/or therapy.

Pulse generators (PGs) are battery-powered medical devices that are implanted in patients and provide electrical pulses (therapy) to stimulate or shock the patient's heart. PGs include cardiac rhythm management (CRM) devices, such as pacemakers, heart failure devices, and defibrillators. One or more remote sensors may be under the control of the PG to provide information that may be used to determine whether to administer therapy to the patient. A battery may serve as the power source in each of the sensors, providing power to, for example, measure physiological parameters and transmit data related to the measured parameters via telemetry. Accurate determination of a battery charge of a remote device supports an effective assessment of the appropriate replacement or recharge time.

SUMMARY

The present invention relates to determining a remaining charge capacity of a battery. The battery has an initial charge capacity and powers a device that includes an active state, during which the device performs at least one function, and an inactive state, during which the device performs no functions. In some embodiments, the remote IMD is activated from the inactive state to perform one or more functions. Data related to the one or more functions is received from the remote IMD, and the remote IMD is returned to the inactive state. An active state charge consumption is computed based on stored parameters associated with an operational charge consumption for each function. An inactive state charge consumption is also computed based on a leakage current associated with the inactive state and a time the device is in the inactive state. The active state charge consumption and inactive state charge consumption are then subtracted from the initial charge capacity.

In another embodiment of the present invention, a system monitors a remaining charge capacity of a battery in an implantable device. The battery has an initial charge capacity. The implantable device includes an active state, during which the implantable device performs at least one function, and an inactive state, during which the implantable device performs no functions. A memory stores parameters associated with charge consumption for each function and a leakage current associated with the inactive state. A processor determines an active state charge consumption based on the stored parameters and an inactive state charge consumption based on the stored leakage current and a time the device is in the inactive state. The processor then subtracts the active state charge consumption and inactive state charge consumption from the initial charge capacity to determine the remaining charge capacity.

In a further embodiment of the present invention, a cardiac rhythm management system includes a remote physiological sensor powered by a battery having an initial charge capacity, and a pulse generator configured to communicate with the remote physiological sensor via telemetry. The remote physiological sensor includes an active state, during which the remote physiological sensor performs at least one function, and an inactive state, during which no functions are performed by the remote physiological sensor. The pulse generator includes a memory operable to store parameters associated with charge consumption for each function performed by the remote physiological sensor and a leakage current associated with the inactive state. The pulse generator also includes a processor operable to determine an active state charge consumption based on the stored parameters and an inactive state charge consumption based on the stored leakage current and a time the device is in the inactive state. The processor is also operable to subtract the active state charge consumption and inactive state charge consumption from the initial charge capacity to determine the remaining charge capacity of the battery.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
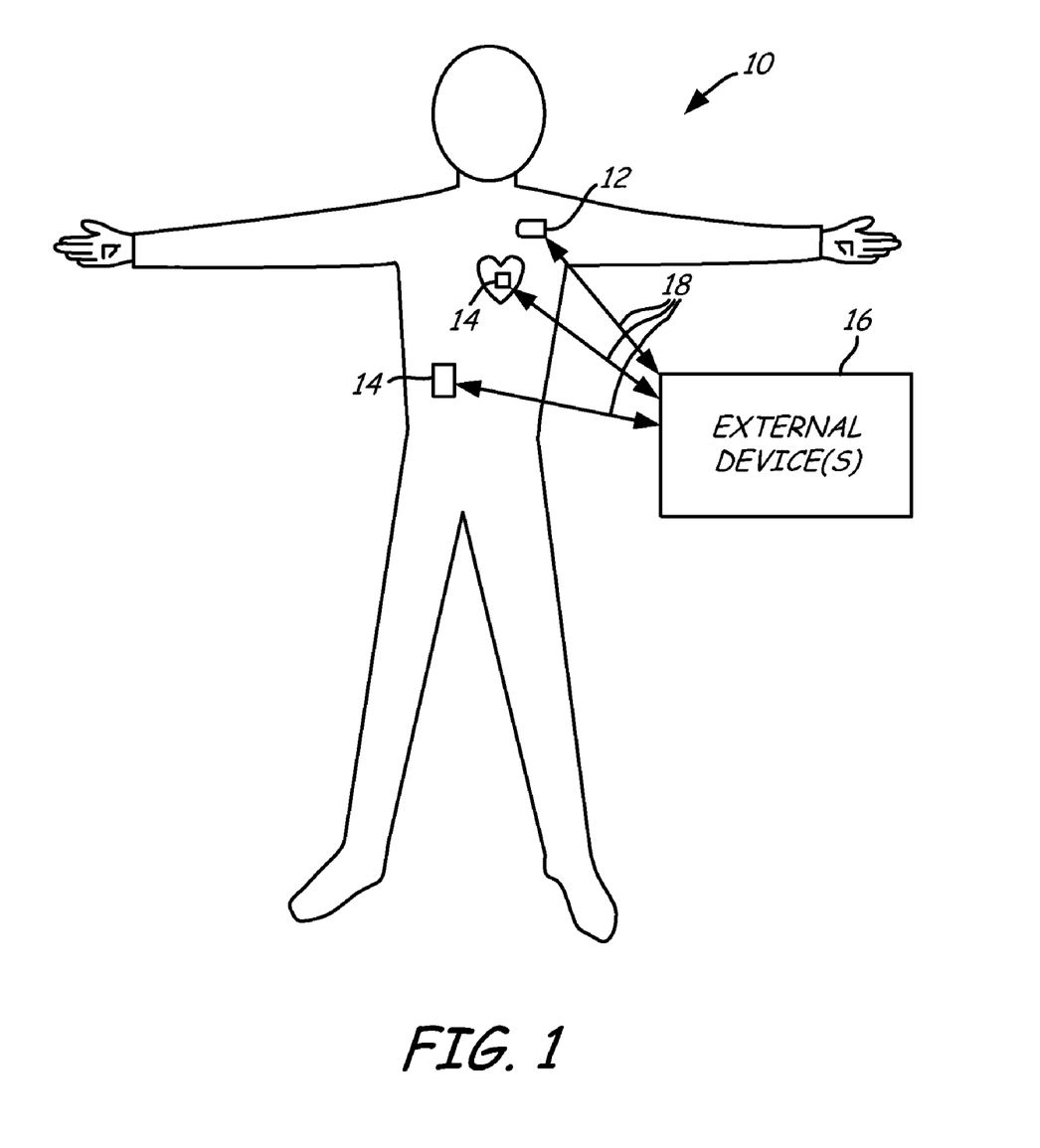
FIG. 1 is a simplified diagram of a network of implantable medical devices implanted in a human body according to an embodiment of the present invention.

FIG. 1 illustrates a simplified human body in which system or network 10 of implantable medical devices is implanted. System 10 includes primary IMD 12 and at least one remote IMD 14. Although the primary IMD 12 and remote IMD 14 are shown implanted in specific locations, in practice, either or both of primary IMD 12 and remote IMD 14 may be implanted anywhere in the body. System 10 may also include an external device 16 (e.g., a computing device and/or programming device), which may communicate with primary IMD 12 and/or remote IMD 14 via communication channels 18. Although FIG. 1 illustrates system 10 utilizing two remote IMDs 14, those skilled in the art will appreciate that one or more than two remote IMDs 14 may be used within the scope of the present invention.

Each remote IMD 14 may be configured to perform one or more designated functions, which may include taking one or more physiological measurements and/or delivering a desired therapy. The implantation sites for remote IMDs 14 are determined based on the particular therapeutic needs of the patient. In one embodiment, remote IMD 14 is adapted to be implanted and to measure blood pressure within the patient's pulmonary artery, and to store and/or transmit blood pressure data to primary IMD 12, another IMD, or external device(s) 16. In another embodiment, remote IMD 14 is adapted to deliver a desired therapy (e.g., a pacing and/or defibrillation stimulus) to the patient's heart or cardiovascular system.

Remote IMD 14 includes power supply components (e.g., a battery) for providing electrical power to the various components and/or circuitry for performing the functions described above. Remote IMD 14 is desirably made as small as possible, however, which constrains the space within remote IMD 14 that is available for power supply components. Such space constraints limit the capacity of these power supply components. In an effort to maximize the longevity of remote IMD 14, its power consumption is minimized, and thus, the average power consumption of remote IMD 14 is desirably very low. For example, in one embodiment, size constraints may limit remote IMD 14 to a 100 microamp-hour, non-rechargeable battery. In such a case, the average power consumption of remote IMD 14 must be less than 10.0 nA to provide a 10 year longevity. In other embodiments, the average power consumption goals may be even lower where, for example, the battery is significantly smaller and/or a greater longevity is desired.

In order to achieve this low power consumption, remote IMD 14 is normally in a "sleep" or "sleeping" state (i.e., an inactive state) characterized by a power consumption of from essentially zero (i.e., a completely powered off state) to a low power state in which only a minimal circuitry (e.g., a timer or comparator) are energized and consuming electrical power. Remote IMD 14 is awakened (i.e., powered on) to an active state in which it can perform one or more designated functions. The terms "wake," "waking," "wake-up," and "awaken" relate to the operation of powering on or energizing one or more aspects of remote IMD 14 to an active state, such that the awakened portion can perform a designated function.

Remote IMD 14 may be awakened by, for example, primary IMD 12 or external device 16. As discussed in detail below, circuitry within remote IMD 14 is adapted to detect a wake-up field generated by primary IMD 12 or external device 16, and to cause remote IMD 14 to awaken and perform its designated functions. Remote IMD 14 is desirably in the active state only to the extent necessary to perform its designated diagnostic and/or therapeutic function(s), after which time it returns to its inactive, sleep state. Additionally, in some embodiments, to maximize longevity of remote IMD 14, the power consumption of the various circuitry for waking up remote IMD 14 is desirably less than about 10 percent of the total power consumption of the remote IMD 14.

Primary IMD 12 operates, in some embodiments, to wake remote IMD 14 from the sleep state, and may further be configured to direct remote IMD 14 to perform one or more designated functions. In this way, primary IMD 12 functions as a "master" device while remote IMD 14 functions as a "slave" device. Primary IMD 12 itself may also be configured to perform therapeutic functions or to take physiologic measurements. For example, primary IMD 12 may, in some embodiments, be a pulse generator for providing a cardiac pacing and/or defibrillation stimulus. The therapeutic functions are not limited to any particular type and can include, for example, drug delivery therapy, or any other therapy capable of being administered with an IMD. Additionally, primary IMD 12 may be configured to measure physiologic parameters such as blood pressure, temperature, blood or fluid flow, strain, electrical, chemical, or magnetic properties within the body.

It should be noted that neither remote IMD 14 nor primary IMD 12 are limited to any particular type or types of devices. For example, remote IMD 14 can be any IMD that is normally in a sleep state to minimize power consumption and is awakened only as necessary to perform a desired function. Similarly, primary IMD 12 can be any IMD that operates, at least in part, to cause remote IMD 14 to wake from a sleep state. Thus, in this regard, remote IMD 14 may sometimes also function as primary IMD 12 in a given embodiment. That is, remote IMD 14 may be configured such that, in its active state, it can cause another remote IMD 14 to wake and perform one or more desired functions.

Figure 2:
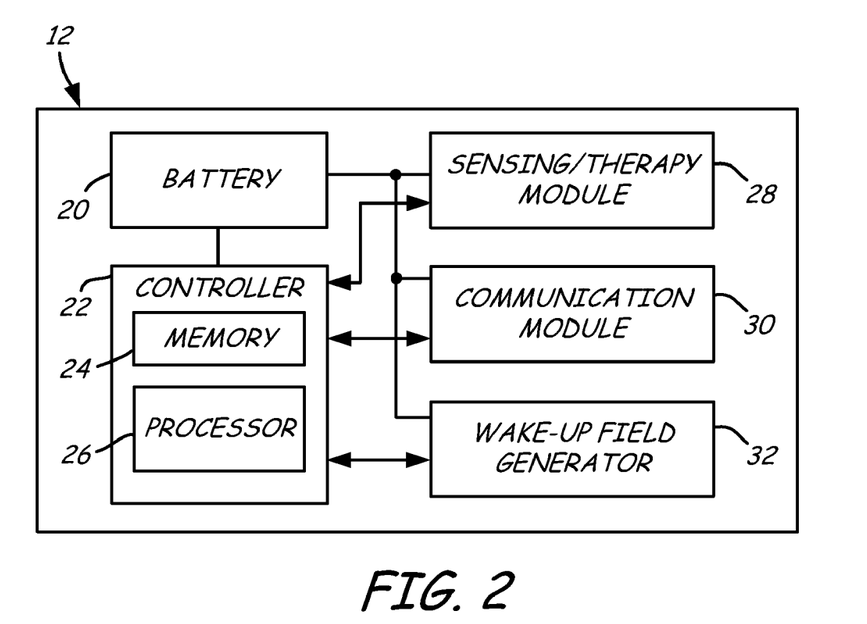
FIG. 2 is a functional block diagram illustrating a primary implantable medical device according to an embodiment of the present invention.

FIG. 2 is a functional block diagram illustrating an embodiment of the primary IMD 12. Primary IMD 12 includes battery 20, primary IMD controller 22, including memory 24 and processor 26, sensing and/or therapy module 28, communication module 30, and wake-up field generator 32. In some embodiments, the primary IMD 12 may not include the sensing and/or therapy module 28. The term "module" is not intended to imply any particular structure. Rather, "module" may mean components and circuitry integrated into a single unit as well as individual, discrete components and circuitry that are functionally related.

Battery 20 operates to provide operating power to controller 22, sensing and/or therapy module 28, communication module 30, and wake-up field generator 32. Controller 22 operates to control sensing and/or therapy module 28, communication module 30, and wake-up field generator 32, all of which are operatively coupled to and communicate with the controller 22. For example, controller 22 may command sensing and/or therapy module 28 to deliver a desired therapy, such as a pacing or defibrillation stimulus. In addition, controller 22 may command communication module 30 to transmit and/or receive data from external device 16 or remote IMDs 14. Furthermore, controller 22 may command wake-up field generator 32 to generate a field (e.g., electromagnetic, magnetic, E-field) that can be detected by a sensor in remote IMD 14, as discussed in detail below.

Controller 22 includes processor 26, which may be a microprocessor or microcontroller, coupled to memory 24, which may include operating instructions and/or software for processor 26. In addition, memory 24 may store parameters related to current and charge consumption information for primary IMD 12 and remote IMD 14. For example, as will be described in more detail below, memory 24 may store predetermined current and charge consumption information for an active state of remote IMD 14, during which remote IMD 14 performs at least one function, and an inactive state of remote IMD 14, during which remote IMD 14 is in the sleep state and performs no functions.

Primary IMD 12 may also include timing circuitry (not shown) which operates to schedule, prompt, and/or activate primary IMD 12 to perform various activities. For example, in one embodiment, the timing circuitry may be utilized to determine the appropriate time at which one or more remote IMDs 14 should wake in order to perform a designated function. In one embodiment, the timing circuitry may be an internal timer or oscillator, while in other embodiments, timing may be performed by specific hardware components that contain hardwired logic for performing the steps, or by any combination of programmed computer components and custom hardware components.

Communication module 30 is configured to allow primary IMD 12 to communicate with other devices, such as external device 16 or remote IMD 14. In one embodiment, primary IMD 12 may communicate with other devices via a wireless connection. Various types of wireless communication that may be used include, but are not limited to, ultrasonic waves, acoustic communications, radio frequency communications, and the like. In some embodiments, communication module 30 includes an acoustic transmitter/receiver configured for acoustic telemetry.

Sensing and/or therapy module 28, if present, operates to perform the therapeutic and/or diagnostic functions described above. In one embodiment, sensing and/or therapy module 28 delivers a cardiac pacing and/or defibrillation stimulus. Again, sensing and/or therapy module 28 is not limited to performing any particular type of physiologic measurement or therapy.

Wake-up field generator 32 operates to generate a field (i.e., a wake-up field) that can be detected by a sensing module in remote IMD 14 for the purpose of causing remote IMD 14 to wake from the sleep state. Various types of wake-up fields may be used, including electromagnetic, magnetic, and electric fields. The particular type of wake-up field utilized will depend on variables such as the available power supply and the implantation site(s) of primary IMD 12 and remote IMDs 14, and their proximity to one another.

Figure 3:
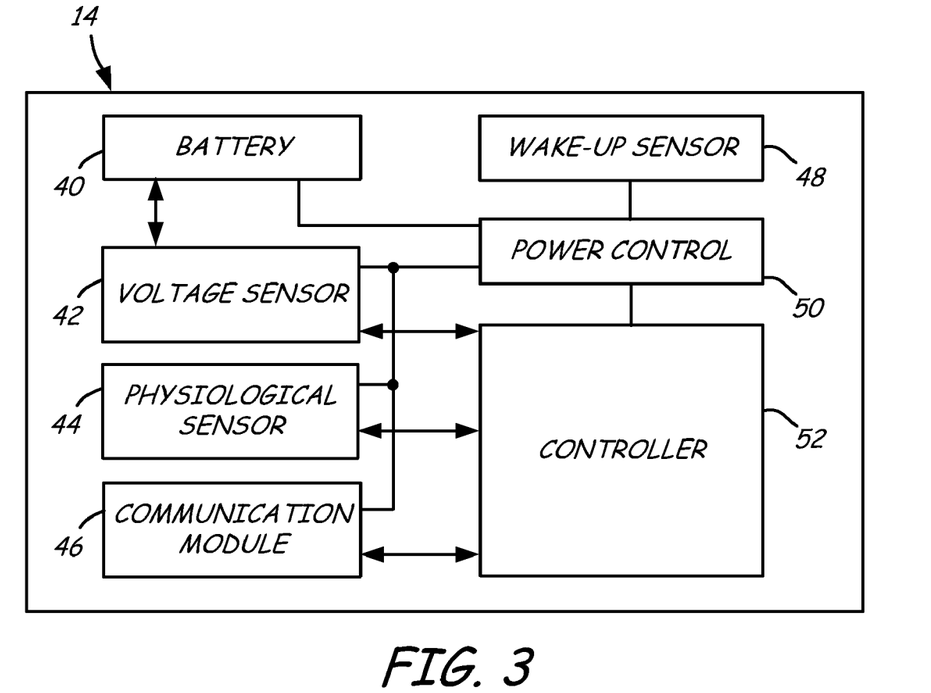
FIG. 3 is a functional block diagram illustrating a remote implantable medical device according to an embodiment of the present invention.

FIG. 3 is a functional block diagram illustrating an embodiment of remote IMD 14. Remote IMD 14 includes battery 40, voltage sensor 42, physiological sensor 44, communication module 46, wake-up sensor 48, power control circuitry 50, and remote IMD controller 52. Battery 40 may be non-rechargeable or rechargeable. Battery 40 operates to supply power to voltage sensor 42, physiological sensor 44, communication module 46, wake-up sensor 48, and controller 52. Power control circuitry 50 is operatively connected to the battery 40 and the wake-up sensor 48, and operates to regulate the supply of power from the battery 40 to voltage sensor 42, physiological sensor 44, communication module 46, wake-up sensor 48, and controller 52.

Controller 52 may be of substantially the same type as or identical to the controller 22 of primary IMD 12, and may include a microprocessor or microcontroller coupled to a memory device that includes operating instructions and/or software for the microprocessor or microcontroller. Remote IMD 12, and in particular the controller 52, may also include timing circuitry which operates to direct the activities of the remote IMD 14 (e.g., taking and storing physiologic measurements, uploading measurement data) after it has been awakened from its sleep state. Alternatively, remote IMD controller 52 may have reduced functionality as compared to primary IMD controller 22, in embodiments where the functional requirements of remote IMD 52 are less extensive.

Physiological sensor 44 performs functions related to measurement of physiological parameters, and is not limited to any particular type of physiological measurement. For example, physiological sensor 44 may be a pressure sensor adapted to measure internal pressure in a blood vessel. In one such embodiment, remote IMD 14 is implanted in the patient's pulmonary artery, and physiological sensor 44 is adapted to measure blood pressure therein. An example remote IMD 14 operable to measure blood pressure, which is suitable for use in conjunction with the present invention, is disclosed in U.S. patent application Ser. No. 12/464,508, entitled "Implantable Pressure Sensor with Automatic Measurement and Storage Capabilities," which is hereby incorporated by reference.

Remote IMD 14 may also have the capability to perform one or more therapeutic functions (e.g., cardiac pacing, drug delivery) in addition to, or in lieu of, one or more measurement functions. In one such embodiment, remote IMD 14 includes a therapy delivery module and does not include physiological sensor 44.

Communication module 46 operates to allow remote IMD 14 to communicate with other devices, such as external device 16, primary IMD 12, or other remote IMDs 14. As discussed above, remote IMD 14 can communicate with other devices via a wireless connection (i.e., telemetry). As with primary IMD 12, the specific type and/or style of wireless communication that can be used is not limited. For example, ultrasonic waves, acoustic communications, radio frequency communications, and the like may be used by the communication circuitry.

In one embodiment, communication module 46 is an acoustic telemetry module and includes an acoustic transmitter/receiver adapted to transmit and receive acoustic signals to/from primary IMD communication module 30. In one such embodiment, the transmitter/receiver includes an ultrasonic transducer and associated circuitry.

In some embodiments, voltage sensor 42, physiological sensor 44, communication module 46, and controller 52 may be integrated into an integrated circuit, while in other embodiments one or more of these elements may be discrete hardware and circuitry.

Wake-up sensor 48 includes one or more sensors and circuitry adapted to detect and/or to react to the presence of a wake-up field generated by wake-up field generator 32 of primary IMD 12. Wake-up sensor 48 is further adapted to cause, upon detecting the presence of such a wake-up field, physiological sensor 44, communication module 46, and/or controller 52 to be awakened, via power control circuitry 50, as appropriate for performing one or more designated functions such as those described above. In some embodiments, remote IMD 14 is configured such that, upon wake-up sensor 48 detecting a wake-up field, controller 52 is initially awakened. Thereafter, controller 52 directs the subsequent wake-up and operation of the other functional portions (e.g., voltage sensor 42, physiological sensor 44, and/or communication module 46).

When remote IMD 14 is implanted in a patient, it is important to monitor the remaining capacity of battery 40 to continuously ensure that remote IMD 14 has sufficient capacity to measure physiological parameters and/or deliver therapy. Various events associated with remote IMD 14 that reduce the available charge in battery 40 should be taken into consideration to accurately determine the remaining charge capacity of battery 40. For example, each function performed by remote IMD 14 consumes an amount of energy from battery 40. In addition, when remote IMD 14 is in a sleep state, a very small amount of leakage current (e.g., less than 1 nA) may still be consumed from battery 40 by the circuit. Furthermore, when the device comes out of the deep sleep state to perform a function, an amount of current may be consumed by the device. While all of these events that reduce the available charge in battery 40 should be considered, the small size and equilibrium state of battery 40 may prevent accurate in-situ measurement of the charge consumed by these events.

Primary IMD 12 and remote IMD 14 according to the present invention are configured to determine the remaining capacity of battery 40 of remote IMD 14 based on predetermined charge consumption parameters for the various states of remote IMD 14. For example, memory 24 of primary IMD 12 stores information related to the amount of charge consumed by each function of remote IMD 14 when remote IMD 14 is awake (i.e., in the active state). In some embodiments, memory 24 stores information about the amount of current consumed by each function and, for fixed-duration functions, memory 24 stores the amount of charge consumed each time the fixed-duration function is performed. Memory 24 may also store information about the leakage current drawn by remote IMD 14 from battery 40 when remote IMD 14 is in the inactive, sleep state. Furthermore, memory 24 may store current and/or charge consumption information for other types of events that draw energy from battery 40, such as the current or charge consumed to wake remote IMD 14 from the sleep state, or to transmit data from remote IMD 14 via communication module 46. In essence, memory 24 stores predetermined current and/or charge consumption values for all functions or events that consume charge from battery 40. The charge consumption parameters stored in memory 24 are "predetermined" in that they are measured or predicted prior to implantation of remote IMD 14, such as during or after fabrication of remote IMD 14. It should be noted that while the subsequent discussion describes primary IMD 12 as providing the charge monitoring function for battery 40, it will be appreciated that other devices may also be adapted to perform this function, including external device 16 (FIG. 1).

Examples of functions performed by remote IMD 14 that consume energy from battery 40, and for which memory 24 stores predetermined current and/or charge consumption information, include: waking up to perform a function; performing a function, such as measuring a physiological parameter; transmitting data from remote IMD 14 to another device; measuring voltage information about battery 40; waking up in response to a wake-up field not intended for remote IMD 14; waking up in response to noise around remote IMD 14; and storing information to a memory internal to remote IMD 14. It will be appreciated that this list is only representative, and that memory 24 can store current and/or charge consumption information for any type of function or event performed by remote IMD 14 that consumes charge from battery 40.

Figure 4:
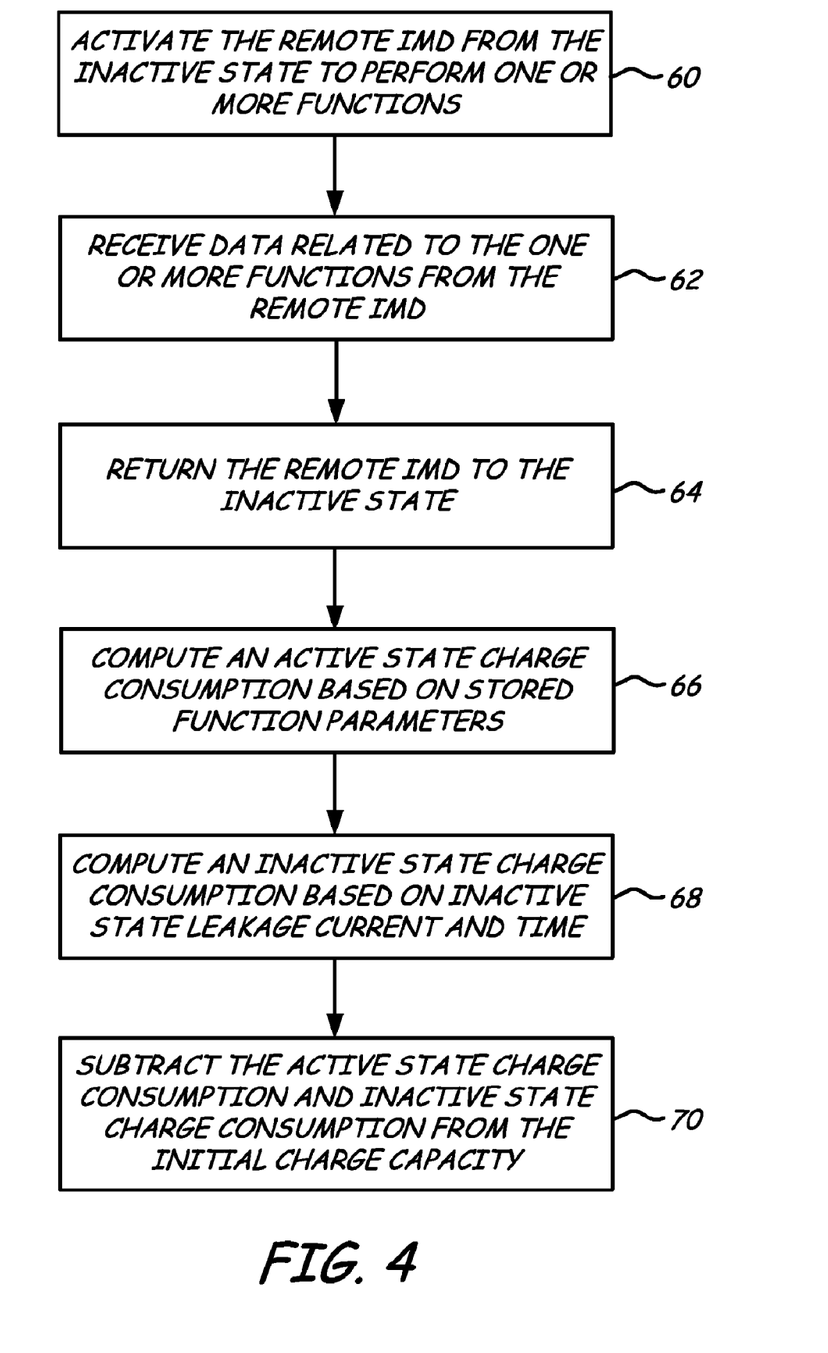
FIG. 4 is a flow diagram of a process for determining a remaining charge capacity of the battery of the remote implantable device of FIG. 3, according to an embodiment of the present invention.

FIG. 4 is a flow diagram of a process for determining a remaining charge capacity of battery 40, in accordance with the principles of the present invention. The initial charge capacity of battery 40 is stored in memory 24. The initial charge capacity represents the charge capacity of battery 40 as most recently determined by primary IMD 12. Immediately after implantation of remote IMD 14, the initial charge capacity stored in memory 24 may be the assumed full charge capacity of battery 40.

In step 60, primary IMD 12 activates remote IMD 14 from the inactive (sleep) state to the active state to perform one or more functions. Primary IMD 12 generates a wake-up field via wake-up field generator 32, which is sensed by wake-up sensor 48 of remote IMD 14. Primary IMD 12 then communicates instructions to remote IMD 14 related to the function or functions that remote IMD 14 is to perform while awake. In an alternative embodiment, remote IMD 14 automatically awakens periodically to perform one or more functions based on, for example, timing signals internal to remote IMD 14.

In step 62, primary IMD 12 receives data related to the one or more functions from remote IMD 14. Remote IMD 14 may transmit the data after each function is performed, or remote IMD 14 may store the data related to the functions for later transmission to primary IMD 12. The data related to the functions performed remote IMD 14 may include, for example, physiological parameter measurement data (e.g., blood pressure data) and a duration of the function. Other information received by primary IMD 12 may include the type of function performed by remote IMD 14 and voltage measurement data as sensed by voltage sensor 42.

In step 64, remote IMD 14 returns to the inactive state. This may occur automatically after remote IMD 14 performs the functions it was awakened to perform. Remote IMD 14 may also return to the inactive state in response to a signal from primary IMD 12.

In step 66, processor 26 of primary IMD 12 computes the charge consumed by remote IMD 14 during the active state based on the stored information in memory 24. For example, for functions having a fixed duration, memory 24 stores data about the charge consumed by the fixed-duration functions each time they are performed by remote IMD 14. Consequently, the charge consumption is calculated by multiplying the stored operational charge consumption information associated with each fixed-duration function by the number of occurrences of the function during the active state. This can be expressed as:

$$Q_{fixed} = x_{f1}Q_{f1} + \ldots + x_{fn}Q_{fn} \quad (1)$$

where $x_{fn}$ represents the number of occurrences of fixed-duration function n, $Q_{fn}$ represents the charge consumed by each occurrence of fixed-duration function n, and $Q_{fixed}$ is the total charge consumed by fixed-duration functions.

For functions having a variable duration, memory 24 stores information about the current consumed of the variable-duration function while it is active. Processor 26 then multiplies the stored information associated with the variable-duration function by the time the variable-duration function is active during the active state. Stated differently, processor 26 integrates the current consumed by the variable-duration function over the time the variable-duration function is active to determine the charge consumed. This can be expressed as:

$$Q_{var} = \int_{t_0}^{t} I_{v1}\, dt + \ldots + \int_{t_0}^{t} I_{vn}\, dt \quad (2)$$

where $I_{vn}$ represents the current consumed by variable-duration function n when performed, and $Q_{var}$ is the total charge consumed by variable-duration functions.

The charge consumed by remote IMD 14 during the active state is thus the total of the charge consumed by the fixed-duration duration functions and variable-duration functions performed during the active state:

$$Q_{active} = Q_{fixed} + Q_{var} \quad (3)$$

In step 68, processor 26 of primary IMD 12 computes the charge consumed by remote IMD 14 during the inactive state based on leakage current information stored in memory 24.

As stated above, the leakage current consumed by remote IMD 14 while in the inactive state is determined prior to implantation of remote IMD 14. Processor 26 thus determines the charge consumed by remote IMD 14 in the inactive state by multiplying the stored leakage current information by the time remote IMD 14 is in the inactive state. Stated differently, processor 26 integrates the leakage current over the time remote IMD 14 is in the inactive state:

$$Q_{inactive} = \int_{t_0}^{t_1} I_{static}\, dt + \ldots + \int_{t_x}^{t_y} I_{static}\, dt. \quad (4)$$

Equation 4 takes into account that the time during which remote IMD 14 is in the inactive state may be separated by times during which remote IMD 14 is in the active state.

The total charge consumed from battery 40 by remote IMD 14 is the sum of the active state charge consumption (expressed in equation 3) and the inactive state charge consumption (expressed in equation 4):

$$Q_{consumed} = Q_{active} + Q_{inactive} \quad (5).$$

In step 70, processor 26 determines the remaining charge capacity of battery 40 by subtracting the active state charge consumption computed in step 66 and the inactive state charge consumption calculated in step 68 from the initial charge capacity stored in memory 24:

$$Q_{remaining} = Q_{initial} - Q_{consumed} \quad (6)$$

The remaining charge capacity is then stored in memory 24, and becomes the new initial charge capacity when the remaining charge capacity is next calculated. The remaining charge capacity may be transmitted to external device(s) 16 for review and analysis by a medical professional.

The frequency at which the remaining charge capacity stored in memory 24 is updated may also be programmed into controller 22. For example, controller 22 may update the remaining charge capacity periodically, such that the total charge consumed from battery 40 over a period of time is subtracted from the initial charge capacity stored in memory 24 to determine the remaining charge capacity. Controller 22 may alternatively update the remaining charge capacity after the occurrence of an event, such as after each time remote IMD 14 returns to the inactive state (step 64). Controller 22 may also continuously update the remaining charge capacity stored in memory 24 in real-time. Controller 22 may also store a running total of the total charge consumed by remote IMD 14 from implantation and compare this total to the charge capacity of battery 40 at implantation to determine the remaining charge capacity.

The remaining charge available from battery 40 is oftentimes closely related to the voltage of battery 40. Thus, the voltage of battery 40 may also be monitored to ensure an accurate assessment of the amount of charge remaining in battery 40. Remote IMD 14 includes voltage sensor 42 operable to generate signals related to the voltage of battery 40. Primary IMD 12 may wake remote IMD 14 and command remote IMD 14 to measure the voltage of battery 40. Primary IMD 12 may be programmed to perform this action periodically or on aperiodic occasions. Alternatively, remote IMD 14 may be programmed to automatically awaken and measure the voltage of battery 40. In any case, remote IMD 14 transmits the voltage measured by voltage sensor 42 to primary IMD 12. Remote IMD 14 may then return to the inactive, sleep state. In some embodiments, the amount of current or charge consumed by remote IMD 14 to perform this measurement and transmit the data is also stored in memory 24.

Primary IMD 12 may then determine the amount of charge consumed by remote IMD 14 based on the voltage of battery 40. In some embodiments, memory 24 stores an algorithm executed by processor 26 for calculating the remaining charge capacity of battery 40 based on the measured voltage of battery 40. In other embodiments, a battery voltage profile is stored in memory 24 that correlates a measured voltage of battery 40 to the remaining charge capacity of battery 40.

Figure 5:
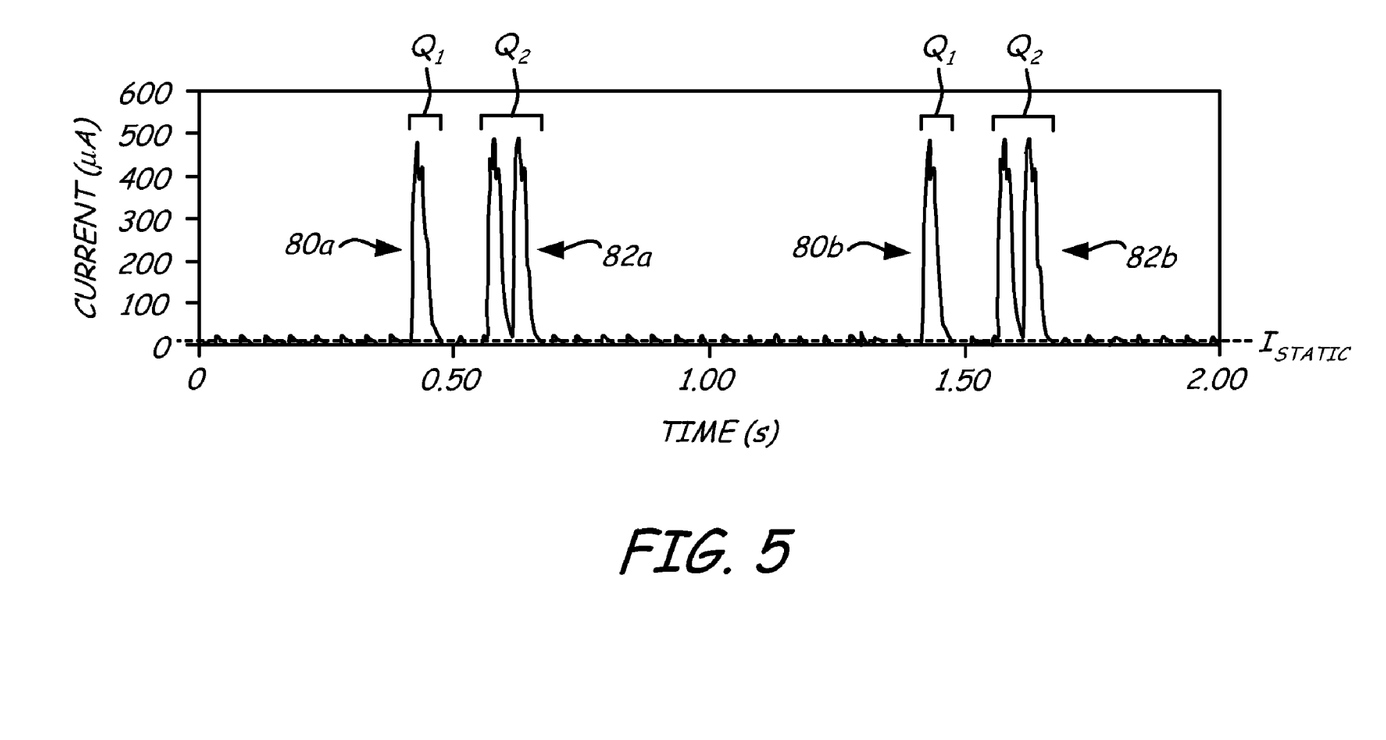
FIG. 5 is a graph showing current consumption of the remote implantable medical device of FIG. 3 during active and inactive states.

FIG. 5 is a graph illustrating a representative current consumption during active and inactive states of remote IMD 14 over a period of two seconds. During the period illustrated, remote IMD 14 is primarily in the inactive (sleep) state, during which remote IMD 14 consumes an average leakage current $I_{static}$. Remote IMD 14 also performs two functions, twice each, during the period illustrated. More particularly, current events 80a and 80b illustrate the current consumption when remote IMD 14 performs a first function, and current events 82a and 82b illustrate the current consumption when remote IMD 14 performs a second function. The current consumption shown is merely for illustration and it will be appreciated that remote IMD 14 can be in any combination of active and inactive states during the same period of time.

To calculate the charge consumed from battery 40 during the period shown, primary IMD 12 retrieves predetermined current and/or charge consumption information corresponding to the first and second functions, as well as the predetermined inactive state leakage current $I_{static}$, from memory 24 to determine the total charge consumed by remote IMD 14 during the period shown. In the example shown in FIG. 5, the first and second functions are each fixed-time functions. As described above, the charge consumed by fixed-time functions is stored in memory 24. Consequently, primary IMD 12 charge consumed by each of the first and second functions is stored in memory 24. The first function consumes a charge of $Q_1$ and the second function consumes a charge of $Q_2$.

The total charge consumed by remote IMD 14 during the period shown can then be calculated pursuant to equations 1-6 above. In particular, pursuant to equation 1, the total charge consumed by remote IMD 14 during the active state is $2Q_1 + 2Q_2$. Pursuant to equation 4, the total charge consumed by remote IMD 14 during the inactive state is the product of $I_{static}$ and the total time remote IMD 14 is in the inactive state. The total charge consumption over the period shown is the total active state and inactive state charge consumption, pursuant to equation 5. The remaining charge of battery 40 can then be computed pursuant to equation 6, and then stored in memory 24 and, optionally, transmitted to external device(s) 16.

In summary, the present invention relates to determining a remaining charge capacity of a battery. The battery has an initial charge capacity and powers a device that includes an active state, during which the device performs at least one function, and an inactive state, during which the device performs no functions. In some embodiments, the remote IMD is activated from the inactive state to the active state to perform one or more functions. Data related to the one or more functions is received from the remote IMD, and the remote IMD is returned to the inactive state. An active state charge consumption is computed based on stored parameters associated with an operational charge consumption for each function. An inactive state charge consumption is also computed based on a leakage current associated with the inactive state and a time the device is in the inactive state. The active state charge consumption and inactive state charge consumption are then subtracted from the initial charge capacity. The present invention allows for an accurate determination of the remaining charge of the remote IMD battery without having to conduct in-situ measurements of the battery charge.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A cardiac rhythm management system comprising:
a remote physiological sensor powered by a battery having an initial charge capacity, wherein the remote physiological sensor includes an active state, during which the remote physiological sensor performs at least one function, and an inactive state, during which no functions are performed by the remote physiological sensor, the remote physiological sensor configured to transmit data related to a voltage of the battery; and
a pulse generator configured to communicate with the remote physiological sensor via telemetry, wherein the pulse generator includes a memory configured to store parameters associated with charge consumption for each function performed by the remote physiological sensor and a leakage current associated with the inactive state, wherein the pulse generator further includes a processor configured to determine an active state charge consumption based on the stored parameters and an inactive state charge consumption based on the stored leakage current and a time the device is in the inactive state, the processor further configured to subtract the active state charge consumption and inactive state charge consumption from the initial charge capacity to determine an estimated remaining charge capacity of the battery, the processor further configured to periodically receive the data related to the voltage of the battery from the remote physiological sensor and determine a verifying remaining charge capacity based on the voltage of the battery, wherein the processor is further configured to compare the estimated remaining charge capacity to the verifying remaining charge capacity to ensure accuracy of the estimated remaining charge capacity.

2. The cardiac rhythm management system of claim 1, wherein the memory is configured to store operational charge consumption information for a function having a fixed duration.

3. The cardiac rhythm management system of claim 1, wherein, for a function having a fixed duration, the memory is configured to store information related to an amount of charge consumption of the fixed-duration function, and wherein the processor is configured to multiply the stored information associated with the fixed-duration function by a number of occurrences of the fixed-duration function during the active state to determine the active state charge consumption.

4. The cardiac rhythm management system of claim 1, wherein, for a function having a variable duration, the memory is configured to store information related to a current consumption of the variable-duration function, and wherein the processor is configured to multiply the stored information associated with the variable-duration function by a time the variable-duration function is active during the active state to determine the active state charge consumption.

5. The cardiac rhythm management system of claim 1, wherein the pulse generator is further configured to communicate battery status information for the remote physiological sensor to a remote computer.

6. A method for monitoring a remaining charge capacity of a battery having an initial charge capacity, wherein the battery powers a remote implantable medical device (IMD) that includes an active state, during which the remote IMD performs at least one function, and an inactive state, during which the remote IMD performs no functions, the method comprising:
activating the remote IMD from the inactive state to perform one or more functions;
receiving data related to the one or more functions from the remote IMD;
returning the remote IMD to the inactive state;
computing an active state charge consumption based on stored parameters associated with an operational charge consumption for each function;
computing an inactive state charge consumption based on a leakage current associated with the inactive state and a time the remote IMD is in the inactive state;
subtracting the active state charge consumption and inactive state charge consumption from the initial charge capacity to determine an estimated remaining charge capacity;
receiving data related to a voltage of the battery periodically;
calculating a verifying remaining charge capacity of the battery based on the voltage of the battery; and
comparing the estimated remaining charge capacity to the verifying remaining charge capacity to ensure accuracy of the estimated remaining charge capacity.

7. The method of claim 6, wherein, for a function having a fixed duration, determining the active state charge consumption comprises:
multiplying stored operational charge consumption information associated with the fixed-duration function by a number of occurrences of the fixed-duration function during the active state.

8. The method of claim 6, wherein, for a function having a variable duration, determining the active state charge consumption comprises:
multiplying stored operational current information associated with the variable-duration function by a time the variable-duration function is active during the active state.

9. A system for monitoring a remaining charge capacity of a battery in an implantable device, wherein the battery has an initial charge capacity, and wherein the implantable device includes an active state, during which the implantable device performs at least one function, and an inactive state, during which the implantable device performs no functions, the system comprising:
a memory configured to store parameters associated with charge consumption for each function and a leakage current associated with the inactive state; and
a processor configured to determine an active state charge consumption based on the stored parameters and an inactive state charge consumption based on the stored leakage current and a time the device is in the inactive state, the processor further configured to subtract the active state charge consumption and inactive state charge consumption from the initial charge capacity to determine an estimated remaining charge capacity, the processor further configured to periodically receive data related to the voltage of the battery from the implantable device and determine a verifying remaining charge capacity based on the voltage of the battery, wherein the processor is further configured to compare the estimated remaining charge capacity to the verifying remaining charge capacity to ensure accuracy of the estimated remaining charge capacity.

10. The system of claim 9, wherein, for a function having a fixed duration, the memory is configured to store information related to an amount of charge consumption of the fixed-duration function, and wherein the processor is configured to multiply the stored information associated with the fixed-duration function by a number of occurrences of the fixed-duration function during the active state to determine the active state charge consumption.

11. The system of claim 9, wherein, for a function having a variable duration, the memory is configured to store information related to a current consumption of the variable-duration function, and wherein the processor is configured to multiply the stored information associated with the variable-duration function by a time the variable-duration function is active during the active state to determine the active state charge consumption.

12. The system of claim 9, and further comprising:
a telemetry module configured to communicate battery status information for the implantable device to a remote computer.

13. The system of claim 9, wherein the memory and the processor are included in a pulse generator.

* * * * *